United States Patent
Takanohashi et al.

(10) Patent No.: US 12,042,777 B2
(45) Date of Patent: Jul. 23, 2024

(54) DEODORANT COMPOSITION SUITABLE FOR ALDEHYDE-BASED GAS OR KETONE-BASED GAS

(71) Applicant: TOAGOSEI CO., LTD., Minato-ku (JP)

(72) Inventors: Atsushi Takanohashi, Nagoya (JP); Yuki Uesugi, Nagoya (JP); Yoshinao Yamada, Nagoya (JP)

(73) Assignee: TOAGOSEI CO., LTD., Minato-ku (JP)

( * ) Notice: Subject to any disclaimer, the term of this patent is extended or adjusted under 35 U.S.C. 154(b) by 642 days.

(21) Appl. No.: 17/287,440

(22) PCT Filed: Nov. 19, 2019

(86) PCT No.: PCT/JP2019/045319
§ 371 (c)(1),
(2) Date: Apr. 21, 2021

(87) PCT Pub. No.: WO2020/121754
PCT Pub. Date: Jun. 18, 2020

(65) Prior Publication Data
US 2021/0387160 A1    Dec. 16, 2021

(30) Foreign Application Priority Data

Dec. 13, 2018 (JP) ................. 2018-233874

(51) Int. Cl.
| | |
|---|---|
| *B01J 20/22* | (2006.01) |
| *A61L 9/014* | (2006.01) |
| *B01J 20/04* | (2006.01) |
| *B01J 20/10* | (2006.01) |
| *B01J 20/18* | (2006.01) |
| *C23F 11/14* | (2006.01) |

(52) U.S. Cl.
CPC ............ *B01J 20/22* (2013.01); *A61L 9/014* (2013.01); *B01J 20/048* (2013.01); *B01J 20/103* (2013.01); *B01J 20/18* (2013.01); *B01J 20/223* (2013.01); *C23F 11/14* (2013.01); *A61L 2209/22* (2013.01)

(58) Field of Classification Search
None
See application file for complete search history.

(56) References Cited

U.S. PATENT DOCUMENTS

| | | | |
|---|---|---|---|
| 4,479,917 A * | 10/1984 | Rothgery ................ | C02F 1/20 252/178 |
| 6,045,784 A | 4/2000 | Ruebusch et al. | |
| 6,136,303 A | 10/2000 | Ruebusch et al. | |
| 6,913,711 B2 | 7/2005 | McKie et al. | |
| 8,679,468 B2 * | 3/2014 | Nakao ................ | C08K 5/098 424/641 |
| 9,302,023 B2 | 4/2016 | Ando et al. | |
| 2002/0125462 A1 | 9/2002 | McKie et al. | |
| 2012/0195845 A1 * | 8/2012 | Hirukawa ................ | B01J 20/22 424/76.2 |
| 2015/0023903 A1 * | 1/2015 | Ando ................ | D06M 13/422 424/76.21 |
| 2017/0036187 A1 * | 2/2017 | Sugiura ................ | A61L 9/01 |
| 2018/0177906 A1 * | 6/2018 | Sugiura ................ | A61L 9/014 |

FOREIGN PATENT DOCUMENTS

| | | |
|---|---|---|
| CN | 101222944 A | 7/2008 |
| EP | 3 308 853 A1 | 4/2018 |
| JP | 2002-513745 A | 5/2002 |
| JP | 2008-259804 A | 10/2008 |
| JP | 2009-19184 A | 1/2009 |
| JP | 2017-567 A | 1/2017 |
| WO | WO 99/56717 A1 | 11/1999 |
| WO | WO 2004/058311 A1 | 7/2004 |
| WO | WO 2006/046611 A1 | 5/2006 |
| WO | WO 2013/057791 A1 | 4/2013 |
| WO | WO 2013/118714 A1 | 8/2013 |
| WO | WO 2016/199756 A1 | 12/2016 |

OTHER PUBLICATIONS

CN 108218515 A (English Abstract). (Date Jun. 29, 2018).*
Japanese Office Action issued Nov. 22, 2022 in Japanese Patent Application No. 2020-559888 (with unedited computer generated English Translation), 8 pages.
Notice of Reasons for Refusal issued May 2, 2023 in Japanese Patent Application No. 2020-559888 (with English machine translation), 10 pages.
Combined Chinese Office Action and Search Report issued Aug. 16, 2022, (Client received on Sep. 2, 2022) in corresponding Chinese Patent Application No. 201980057591.7 (with English Translation and English Translation of Category of Cited Documents), 15 pages.
International Search Report issued on Feb. 4, 2020 in PCT/JP2019/045319 filed on Nov. 19, 2019, 3 pages.
Extended European Search Report issued Jul. 25, 2022, in corresponding European Patent Application No. 19897004.8, 9 pages.
Combined Chinese Office Action and Search Report issued May 11, 2023, in corresponding Chinese Patent Application No. 201980057591.7 (with English Translation), 14 pages.
Combined Taiwanese Office Action and Search Report issued May 22, 2023, in corresponding Taiwanese Patent Application No. 108143907 (with English Translation), 13 pages.
Chinese Office Action issued Dec. 2, 2022 in Chinese Patent Application No. 201980057591.7 (with unedited computer-generated English Translation), 12 pages.

(Continued)

*Primary Examiner* — Joseph D Anthony
(74) *Attorney, Agent, or Firm* — Oblon, McClelland, Maier & Neustadt, L.L.P.

(57) ABSTRACT

A deodorant composition may be suitable for use with an aldehyde gas or a ketone gas, and may include an aminoguanidine salt and a metal chelating agent. The aminoguanidine salt is preferably at least one of an aminoguanidine hydrochloride and an aminoguanidine sulfate. The chelating agent is preferably at least one of an inorganic phosphoric acid and salt thereof, and a carboxylic acid and salt thereof.

12 Claims, No Drawings

(56) References Cited

OTHER PUBLICATIONS

Taiwanese Office Action issued Jan. 30, 2024 in Taiwanese Patent Application No. 108143907 received Feb. 16, 2024 (with English translation), 9 pages.

* cited by examiner

DEODORANT COMPOSITION SUITABLE FOR ALDEHYDE-BASED GAS OR KETONE-BASED GAS

TECHNICAL FIELD

The present invention relates to a deodorant composition suitable for deodorizing an aldehyde gas or a ketone gas whose corrosion is suppressed when stored in a container made of a metal (including an alloy; hereinafter the same applies). Further, the present invention relates to a deodorant composition suitable for an aldehyde gas or a ketone gas, in which corrosion of a container, a member, and the like is suppressed when a processing liquid containing a deodorant composition, which is a raw material for producing a deodorant product, an adhesive resin, and the like is produced by using an apparatus provided with a metal container, a stirring blade, etc. and when the processing liquid is used to produce a deodorant product.

BACKGROUND ART

Various gaseous pollutants such as foul odors and harmful gases exist in the air depending on living environment, work environment, etc., and there is a growing interest in removing these gaseous pollutants and obtaining a comfortable environment. For example, aldehyde gas and ketone gas are contained in various odors such as cigarette smoke, body odor (e.g., sweat odor and oral odor), pet odor, mold odor, paint odor, and print odor, and the effect on the human body has been pointed out. Therefore, in recent years, deodorant products such as a deodorizing filter material and a deodorant filter for purifying air containing aldehyde gas or ketone gas indoors and in automobiles and the like have been proposed. Various aldehyde gas deodorants and ketone gas deodorants are known as raw materials for producing those deodorant products (see Patent Literatures 1 to 4).

Patent Literature 1 discloses an aldehyde gas deodorant in which at least one selected from a group consisting of succinic dihydrazide, carbohydrazide, and oxalic acid dihydrazide is supported by at least one selected from a group consisting of a silicate compound and a tetravalent metal phosphate.

Patent Literature 2 discloses an aldehyde gas deodorant containing at least one selected from a group consisting of monoaminoguanidine salt, diaminoguanidine salt and tri-aminoguanidine salt.

Patent Literature 3 discloses an aldehyde gas deodorant obtained by a step of preparing a deodorant composition containing a dihydrazide compound, a hydrous inorganic powder, and water, and a step of heating the deodorant composition at a temperature of 45° C. or higher and 90° C. or lower so that 4.5% by mass or more of water remains in the entire deodorant.

Patent Literature 3 furthermore discloses a deodorant processed product (deodorant product) obtained by post-processing an aldehyde gas deodorant using a binder. In this case, a processing liquid containing an aldehyde gas deodorant, a binder, and a liquid medium is usually used.

Patent Literature 4 discloses a ketone gas adsorbent characterized by containing a primary amine compound.

PRIOR TECHNICAL ART

Patent Literature

Patent Literature 1: WO 2004/58311
Patent Literature 2: WO 2006/46611
Patent Literature 3: WO 2013/118714
Patent Literature 4: WO 2016/199756

SUMMARY OF INVENTION

Technical Problems

In recent years, although deodorants mainly composed of aminoguanidine salt have been widely used as deodorants for aldehyde gas and ketone gas, when a storage container for such a deodorant contains metal or when manufacturing equipment (container, stirring blade, etc.) for preparing a processing liquid that is used for producing a deodorant product and contains a deodorant, an adhesive resin, etc. contains metal, corrosion that seems to be caused by the aminoguanidine salt has been sometimes confirmed. Due to such corrosion, the deodorant or processing liquid mainly composed of aminoguanidine salt contain impurities, or the corrosion causes problems in the manufacturing equipment. Therefore, improvement of deodorant has been desired for stable production of deodorant products.

Solutions to Problems

The present inventors have found that the above-mentioned problems can be solved by using an aminoguanidine salt and a metal chelating agent (metal ion chelating agent) together.

The deodorant composition used for an aldehyde gas or a ketone gas in the present invention (hereinafter, may be simply referred to as "deodorant composition") is as follows.

[1] A deodorant composition used for an aldehyde gas or a ketone gas, characterized by including an aminoguanidine salt and a metal chelating agent (hereinafter, simply referred to as "chelating agent").

[2] The deodorant composition used for an aldehyde gas or a ketone gas according to [1] above, wherein the aminoguanidine salt is at least one selected from a group consisting of an aminoguanidine hydrochloride and an aminoguanidine sulfate.

[3] The deodorant composition used for an aldehyde gas or a ketone gas according to [1] or [2] above, wherein the chelating agent is at least one selected from a group consisting of an inorganic phosphoric acid and salt thereof, and a carboxylic acid and salt thereof.

[4] The deodorant composition used for an aldehyde gas or a ketone gas according to any one of [1] to [3] above, wherein at least one of the aminoguanidine salt and the chelating agent is supported by an inorganic carrier.

[5] The deodorant composition used for an aldehyde gas or a ketone gas according to [4] above, wherein the inorganic carrier is consisting of a silicon compound.

[6] The deodorant composition used for an aldehyde gas or a ketone gas according to any one of [1] to [5] above, wherein a content of the chelating agent is in a range from 1 to 50 parts by mass based on 100 parts by mass of a content of the aminoguanidine salt.

[7] The deodorant composition used for an aldehyde gas or a ketone gas according to any one of [1] to [6], wherein a content ratio of the aminoguanidine salt is in a range from 5% to 70% by mass with respect to the entire composition.

Advantageous Effects of Invention

The deodorant composition of the present invention is useful for producing a deodorant product suitable for deodorizing the aldehyde gas and/or the ketone gas. When a container, a stirring blade or stirring shaft of a stirring device, and the like, used for storing or producing (1) a deodorant composition, (2) a processing liquid that is used for producing a deodorant product containing the deodorant composition and contains the deodorant composition, an adhesive resin, and a dispersion medium, or (3) a slurry containing the deodorant composition and the dispersion medium, are made of metal, corrosion can be suppressed. Therefore, it is possible to efficiently produce a deodorant product in which mixing of impurities due to corrosion is suppressed. In particular, in a case where a content of the chelating agent is in a range from 1 to 50 parts by mass when a content of the aminoguanidine salt is 100 parts by mass, the above effect becomes remarkable.

DESCRIPTION OF EMBODIMENT

The present invention is a deodorant composition suitable for an aldehyde gas and/or a ketone gas, which utilizes a chemical adsorption of the aldehyde gas and/or the ketone gas on an aminoguanidine salt. The deodorant composition is a composition including the aminoguanidine salt and a chelating agent, and is a solid composition which may further include other components (described later). The aldehyde gas means a gas derived from a compound having an aldehyde group, and is specifically a gas derived from formaldehyde, acetaldehyde, propanal, butanal, nonenal, and the like. The ketone gas means a gas derived from a compound having a carbonyl group, and is specifically a gas derived from acetone, methyl ethyl ketone, acetoacetic acid, β-hydroxybutyric acid, diacetyl, 2,3-pentanedione, 2,3-hexanedione, and the like. The deodorant composition of the present invention is particularly suitable for the aldehyde gas, but is also a deodorant composition having a deodorizing effect on the ketone gas.

Examples of the aminoguanidine salt include a hydrochloride, a sulfate, a carbonate, and a nitrate of monoaminoguanidine, diaminoguanidine, or triaminoguanidine, and the like.

Examples of the monoaminoguanidine salt include aminoguanidine hydrochloride, aminoguanidine sulfate, aminoguanidine bicarbonate, aminoguanidine nitrate, and the like.

Examples of the diaminoguanidine salt include diaminoguanidine hydrochloride, diaminoguanidine sulfate, diaminoguanidine nitrate, and the like.

Examples of the triaminoguanidine salt include triaminoguanidine hydrochloride and triaminoguanidine nitrate, and the like.

As the aminoguanidine salt, aminoguanidine hydrochloride and aminoguanidine sulfate are preferable.

The aminoguanidine salt contained in the deodorant composition according to the embodiment of the present invention may be used singly or in combination of two or more types thereof.

The chelating agent is not particularly limited as long as it coordinates with a metal ion to form a chelating compound (polydentate ligand). In the embodiment of the present invention, the chelating agent is preferably one that coordinates with a heavy metal ion of iron, chromium, nickel, cobalt, tungsten, manganese, molybdate, zinc, and the like to form a chelating compound. An inorganic phosphoric acid, carboxylic acid, and salts thereof can be used. These compounds may be used in combination. When the chelating agent includes the inorganic phosphoric acid, there is no discoloration of the deodorant composition, being more preferable.

Examples of the inorganic phosphoric acid include phosphoric acid, pyrophosphoric acid, tripolyphosphoric acid, hexametaphosphoric acid, and the like. The salt of inorganic phosphoric acid is a salt of the inorganic phosphoric acid and a monovalent or divalent metal and is preferably a salt of the inorganic phosphoric acid and an alkali metal such as potassium and sodium. The inorganic phosphate is preferably sodium hexametaphosphate.

Examples of the carboxylic acid include a dicarboxylic acid such as succinic acid, glutaric acid, and adipic acid; an aminocarboxylic acid such as nitrilotriacetic acid, ethylenediaminetetraacetic acid, diethylenetriaminopentaacetic acid, and triethylenetetraaminehexacetic acid; a hydroxyaminocarboxylic acid such as dihydroxyethylglycine, N-(2-hydroxyethyl)iminodiacetic acid, triethanolamine L-glutamate diacetic acid, and hydroxyethylethylenediaminetetraacetic acid; a hydroxycarboxylic acid such as citric acid, tartaric acid, gluconic acid, and glucoheptonic acid; and the like. As the carboxylic acid, dicarboxylic acid and hydroxycarboxylic acid are preferable.

The salt of carboxylic acid may be a sodium salt, a potassium salt, a lithium salt, an ammonium salt, an amine salt, an alkanolamine salt, or the like.

Examples of the hydroxycarboxylic acid salt include sodium citrate, sodium tartrate, sodium gluconate, sodium glycoheptonate, and the like. Examples of the aminocarboxylic acid salt include nitrilotriacetic acid•3 sodium, ethylenediaminetetraacetic acid•4 sodium, ethylenediaminetetraacetic acid•2 sodium, diethylenetriaminopentacetic acid•5 sodium, and the like. Examples of the hydroxyaminocarboxylic acid salt include sodium dihydroxyethylglycine, N-(2-hydroxyethyl)iminodiacetic acid•2 sodium, triethanolamine L-glutamate diacctic acid•4 sodium, hydroxyethylethylenediaminetetraacetic acid-4 sodium, and the like.

A content of the chelating agent contained in the deodorant composition according to the embodiment of the present invention is not particularly limited. A content ratio of the chelating agent is preferably in a range from 1 to 50 parts by mass, more preferably from 5 to 45 parts by mass, and further preferably from 10 to 40 parts by mass based on 100 parts by mass of the content of the aminoguanidine salt because the effect of the present invention can be sufficiently obtained while maintaining the deodorizing effect on the aldehyde gas or the ketone gas.

In the deodorant composition according to the embodiment of the present invention, it is preferable that at least one of the aminoguanidine salt and the chelating agent be supported by an inorganic carrier, and it is particularly preferable that the deodorant composition be a composition including a composite (hereinafter, referred to as "composite (1)") formed by supporting at least the aminoguanidine salt with the inorganic carrier.

The inorganic carrier is not particularly limited as long as it does not react with water and is insoluble in water. Examples of the inorganic carrier include a silicon compound, a tetravalent metal phosphate compound, and the like. Among these compounds, a silicon compound is preferable.

Examples of the silicon compound include a silicate compound, zeolite, silica, silica gel, and the like.

Examples of the silicate compound include aluminum silicate, magnesium silicate, and the like.

The aluminum silicate is preferably a compound represented by the following general formula (1), and the magnesium silicate is preferably a compound represented by the following general formula (2).

$$Al_2O_3 \cdot mSiO_2 \cdot nH_2O \quad (1)$$

(In the formula, m is a number greater than or equal to 6 and n is a number greater than or equal to 1.)

$$MgO \cdot qSiO_2 \cdot nH_2O \quad (2)$$

(In the formula, q is a number greater than or equal to 1 and n is a number greater than or equal to 0.1.)

In the general formula (1) representing the aluminum silicate, m is preferably in a range from 6 to 50, and more preferably from 8 to 15. Further, n is preferably in a range from 1 to 20, and more preferably from 3 to 15.

In the general formula (2) representing the magnesium silicate, q is preferably in a range from 1 to 20, and more preferably from 3 to 15. Further, n is preferably in a range from 0.1 to 20, and more preferably from 1 to 8.

As the zeolite, those having structures such as A type, X type, Y type, α type, β type, and ZSM-5 can be used. These may be either natural or synthetic.

Examples of the tetravalent metal phosphate compound include zirconium phosphate, titanium phosphate, tin phosphate, and the like. These compounds may be crystalline or amorphous.

The properties and size of the inorganic carrier are not particularly limited. From a viewpoint of the deodorizing effect on the aldehyde gas or the ketone gas, the BET specific surface area is preferably 10 m$^2$/g or higher, and more preferably 50 m$^2$/g or higher, and an average particle size is preferably in a range from 0.01 to 50 μm, and more preferably from 0.02 to 20 μm.

In the composition containing the composite (1) formed by supporting aminoguanidine salt with the inorganic carrier, which is a preferred aspect of the deodorant composition according to the embodiment of the present invention, content ratios of the aminoguanidine salt and the inorganic carrier constituting the composite (1) is not particularly limited. From a viewpoint of stability of the composite (1) and the deodorizing effect on the aldehyde gas or the ketone gas, the content ratio of the aminoguanidine salt is preferably in a range from 5 to 500 parts by mass, more preferably from 11 to 200 parts by mass, and further preferably from 20 to 100 parts by mass based on 100 parts by mass of a content of the inorganic carrier.

The composite (1) may be obtained by a conventionally known method. Examples of the preparation method include a method of mixing a powder of the aminoguanidine salt and a powder of the inorganic carrier; a method of mixing a solution of the aminoguanidine salt and the powder of the inorganic carrier and then removing a medium; and the like. The method is not limited to these methods.

The deodorant composition according to the embodiment of the present invention may be a composition including a composite (hereinafter, referred to as "composite (2)") formed by supporting a chelating agent with an inorganic carrier. This composite (2) may be produced in the same manner as that for the composite (1).

The deodorant composition according to the embodiment of the present invention may be a composition including a composite (hereinafter, referred to as "composite (3)") formed by supporting both the aminoguanidine salt and chelating agent with an inorganic carrier. In this composite (3), the supported aminoguanidine salt and chelating agent may be in a contact state or in a non-contact state.

The deodorant composition according to the embodiment of the present invention may further include other components. Examples of other components include other deodorants that chemically adsorb an aldehyde gas or a ketone gas (such as hydrazide compounds and azole compounds with an amino group); a solid deodorant that chemically adsorbs a sulfur-based gas, basic gas, organic acidic gas, etc.; and the like. The composite (1), the composite (2), and the composite (3) may have a particle size adjusted by conventionally known disintegration/crushing. Specific methods for disintegration/crushing include, but are not limited to, jet mill crushing, ACM crushing, pin mill crushing, and the like.

A content ratio of the aminoguanidine salt contained in the deodorant composition according to the embodiment of the present invention is preferably in a range from 5% to 70% by mass, more preferably from 10% to 60% by mass, and further preferably from 20% to 5% by mass with respect to the entire composition from a viewpoint of the deodorizing effect on the aldehyde gas or the ketone gas.

When the deodorant composition according to the embodiment of the present invention is stored in a container, a material of the container is usually a resin or a metal. In a case the container is made of a metal, an inner wall surface is not corroded even if the deodorant composition is stored, and then the container can be preferably handled.

The deodorant composition according to the embodiment of the present invention is a suitable production raw material for bonding the deodorant composition to the base material to obtain a deodorant product. Such a deodorant product can be usually produced by applying a slurry (dispersion liquid containing no adhesive resin) containing the deodorant composition of the present invention and a dispersion medium or a processing liquid containing the deodorant composition of the present invention, an adhesive resin, and the dispersion medium to a base material and then drying it.

The dispersion medium used for preparing the slurry or processing liquid may be water, an organic solvent, or a mixed liquid of these.

The slurry or processing liquid may include additives such as a dispersants, a viscosity modifier, a defoamer, a colorant, an antistatic agents a flame retardant, a fragrance, an antibacterial agent, an antiviral agent, an antiallergen agent, and a preservative.

The adhesive resin contained in the processing liquid is not particularly limited, and an ethylene/vinyl acetate copolymer or a modified product thereof, an ethylene/vinyl chloride copolymer or a modified product thereof, a vinyl chloride/vinyl acetate copolymer, polyvinyl acetate, polyvinyl chloride, a modified olefin resin (such as chlorinated polyolefin), a polyester resin, an acrylic resin, a urethane resin or a modified product thereof, a styrene/butadiene copolymer, a styrene/isoprene copolymer, a styrene/butadiene/styrene block copolymer, a styrene/ethylene/butylene/styrene block copolymer, a styrene/ethylene/propylene/styrene block copolymer, a hydrogenated styrene/butadiene/styrene block copolymer, a hydrogenated styrene/ethylene/butylene/styrene block copolymer, a hydrogenated styrene/ethylene/propylene/styrene block copolymer, and the like may be used.

A content ratio of the adhesive resin contained in the processing liquid is usually in a range from 10 to 300 parts by mass based on 100 parts by mass of the deodorant composition of the present invention.

The slurry or processing liquid is preferably an aqueous mixed liquid mainly composed of water as a dispersion medium. A pH of the aqueous mixed liquid is not particularly limited, but is preferably 1 to 7 from a viewpoint of stability. When the slurry or processing liquid composed of the aqueous mixed liquid is produced, an apparatus provided with a container, a stirring blade, etc. for containing and stirring the raw materials is usually used. When the equipment is made of metal, corrosion is suppressed after the production of the slurry or processing liquid even if the pH of the slurry or processing liquid is in the above range. Therefore, when continuous production is performed using the same equipment, the composition of the slurry or processing liquid is stably maintained, so that mass production can be efficiently performed. When a deodorant product is produced using the processing liquid, corrosion in a deodorant product production apparatus is suppressed.

EXAMPLES

Hereinafter, embodiments of the present invention will be described in more detail with reference to Examples, but the present invention is not limited to these Examples. In the following, "part" and "%" are based on weight unless otherwise indicated.

1. Raw Material for Deodorant Composition

The raw material used in the production of the deodorant composition is as follows.

1-1. Aminoguanidine Salt
  (1) Aminoguanidine hydrochloride
  (2) Aminoguanidine sulfate
  These are all reagent powders.

1-2. Chelating Agent
  (1) Sodium hexametaphosphate
  (2) Sodium dihydrogen phosphate
  (3) Succinic acid
  (4) Citric acid
  (5) Ethylene diaminetetraacetic acid•2 sodium
  These are all reagent powders.

1-3. Inorganic Carrier
  (1) Silica particles
  The particles have an average particle size of 5 μm, and a BET specific surface area of 700 m$^2$/g.
  (2) Aluminum Silicate Particles
  The particles are of $Al_2O_3 \cdot 9SiO_2 \cdot H_2O$ and have an average particle size of 10 μm and a BET specific surface area of 600 m$^2$/g.
  (3) Zeolite Particles
  The particles are of ZSM-5 type zeolite and have an average particle size of 6 μm and a BET specific surface area of 350 m$^2$/g.

2. Production and Evaluation of Deodorant Composition

Deodorant compositions (D1) to (D19) having the configurations shown in Table 1 were produced. Depending on types of composition, the deodorant compositions might be produced using an aqueous solution prepared in advance.

Example 1

100 parts of aminoguanidine hydrochloride powder and 11.1 parts of sodium hexametaphosphate powder were mixed to produce the deodorant composition (D1).

Example 2

100 parts of silica particles, 13.2 parts of a 40% aminoguanidine hydrochloride aqueous solution, and 1.3 parts of a 40% sodium hexametaphosphate aqueous solution were mixed, and the mixture was then heated and dried at a temperature of 120° C. for 2 hours to distill off a medium, and thus to produce the solid deodorant composition (D2).

Example 3

100 parts of silica particles, 64.1 parts of a 40% aminoguanidine hydrochloride aqueous solution, and 6.4 parts of a 40% sodium hexametaphosphate aqueous solution were mixed, and the mixture was then heated and dried at a temperature of 120° C. for 2 hours to distill off a medium, and thus to produce the solid deodorant composition (D3).

Example 4

100 parts of silica particles, 182 parts of a 40% aminoguanidine hydrochloride aqueous solution, and 22.7 parts of a 40% sodium hexametaphosphate aqueous solution were mixed, and the mixture was then heated and dried at a temperature of 120° C. for 2 hours to distill off a medium, and thus to produce the solid deodorant composition (D4).

Example 5

100 parts of silica particles, 875 parts of a 40% aminoguanidine hydrochloride aqueous solution, and 125 parts of a 40% sodium hexametaphosphate aqueous solution were mixed, and the mixture was then heated and dried at a temperature of 120° C. for 2 hours to distill off a medium, and thus to produce the solid deodorant composition (D5).

Example 6

100 parts of silica particles, 28.7 parts of a 40% aminoguanidine hydrochloride aqueous solution, and 8.6 parts of a 40% sodium dihydrogen phosphate aqueous solution were mixed, and the mixture was then heated and dried at a temperature of 120° C. for 2 hours to distill off a medium, and thus to produce the solid deodorant composition (D6).

Example 7

100 parts of silica particles, 112 parts of a 40% aminoguanidine hydrochloride aqueous solution, and 56.0 parts of a 8% succinic acid aqueous solution were mixed, and the mixture was then heated and dried at a temperature of 120° C. for 2 hours to distill off a medium, and thus to produce the solid deodorant composition (D7).

Example 8

100 parts of silica particles, 266 parts of a 40% aminoguanidine hydrochloride aqueous solution, and 16.0 parts of a 40% citric acid aqueous solution were mixed, and the mixture was then heated and dried at a temperature of 120° C. for 2 hours to distill off a medium, and thus to produce the solid deodorant composition (D8).

Example 9

100 parts of aluminum silicate particles, 13.4 parts of a 40% aminoguanidine sulfate aqueous solution, and 5.4 parts of a 40% sodium hexametaphosphate aqueous solution were mixed, and the mixture was then heated and dried at a temperature of 120° C. for 2 hours to distill off a medium, and thus to produce the solid deodorant composition (D9).

Example 10

100 parts of aluminum silicate particles, 28.4 parts of a 40% aminoguanidine sulfate aqueous solution, and 5.7 parts of a 40% sodium dihydrogen phosphate aqueous solution were mixed, and the mixture was then heated and dried at a temperature of 120° C. for 2 hours to distill off a medium, and thus to produce the solid deodorant composition (D10).

Example 11

100 parts of aluminum silicate particles, 64.1 parts of a 40% aminoguanidine sulfate aqueous solution, and 32.1 parts of a 8% succinic acid aqueous solution were mixed, and the mixture was then heated and dried at a temperature of 120° C. for 2 hours to distill off a medium, and thus to produce the solid deodorant composition (D11).

Example 12

100 parts of silica particles, 112 parts of a 40% aminoguanidine sulfate aqueous solution, and 11.2 parts of a 40% citric acid aqueous solution were mixed, and the mixture was then heated and dried at a temperature of 120° C. for 2 hours to distill off a medium, and thus to produce the solid deodorant composition (D12).

Example 13

100 parts of zeolite particles, 175 parts of a 40% aminoguanidine sulfate aqueous solution, and 52.6 parts of a 10% EDTA•2 sodium aqueous solution were mixed, and the mixture was then heated and dried at a temperature of 120° C. for 2 hours to distill off a medium, and thus to produce the solid deodorant composition (D13).

Example 14

100 parts of zeolite particles, 28.1 parts of a 40% aminoguanidine hydrochloride aqueous solution, and 2.8 parts of a 40% sodium hexametaphosphate aqueous solution were mixed, and the mixture was then heated and dried at a temperature of 120° C. for 2 hours to distill off a medium, and thus to produce the solid deodorant composition (D14).

Example 15

100 parts of zeolite particles, 66.7 parts of a 40% aminoguanidine hydrochloride aqueous solution, and 16.7 parts of a 40% sodium hexametaphosphate aqueous solution were mixed, and the mixture was then heated and dried at a temperature of 120° C. for 2 hours to distill off a medium, and thus to produce the solid deodorant composition (D15).

Example 16

100 parts of zeolite particles, 125 parts of a 40% aminoguanidine hydrochloride aqueous solution, and 41.7 parts of a 40% sodium hexametaphosphate aqueous solution were mixed, and the mixture was then heated and dried at a temperature of 120° C. for 2 hours to distill off a medium, and thus to produce the solid deodorant composition (D16).

Comparative Example 1

Only the aminoguanidine hydrochloride powder was used as the deodorant composition (D17).

Comparative Example 2

100 parts of silica particles and 62.5 parts of a 40% aminoguanidine hydrochloride aqueous solution were mixed, and the mixture was then heated and dried at a temperature of 120° C. for 2 hours to distill off a medium, and thus to produce the solid deodorant composition (D18).

Comparative Example 3

100 parts of aluminum silicate particles and 42.9 parts of a 40% aminoguanidine sulfate aqueous solution were mixed, and the mixture was then heated and dried at a temperature of 120° C. for 2 hours to distill off a medium, and thus to produce the solid deodorant composition (D19).

The following evaluations were performed on each of the obtained compositions, and the results are also shown in Table 1.

(A) Deodorizing Capacity
(A-1) Deodorizing Capacity of Acetaldehyde Gas 0.01 g of the deodorant composition was stored in a "Smart Bag PA" (trade name), manufactured by GL Sciences Inc., having an internal volume of 5 liters. Subsequently, 3 liters of 750 ppm of an acetaldehyde gas was injected into this resin bag, and the resin bag was sealed and allowed to stand at room temperature. After 24 hours, a concentration of acetaldehyde remaining in the resin bag was measured using a gas detector tube manufactured by GASTEC CORPORATION. Then, the deodorizing capacity (mL/g) was obtained by the following equation (1).

$$\text{Deodorizing capacity (mL/g)} = [(C_0 - C) \times V/W]/1000 \qquad (1)$$

(In the equation, $C_0$ is an initial concentration [ppm] of acetaldehyde gas injected, C is a concentration [ppm] of acetaldehyde gas remaining in the resin bag after 24 hours, V is an amount [L] of acetaldehyde gas injected, and W is an amount [g] of deodorant composition.)

(A-2) Deodorizing Capacity Of Diacetyl Gas

The deodorizing capacity of a diacetyl gas was determined in the same manner as those in (A-1) above except that 300 ppm of a diacetyl gas was used instead of 750 ppm of an acetaldehyde gas.

(A-3) Deodorizing Capacity of Acetone Gas

The deodorizing capacity of a diacetyl gas was determined in the same manner as those in (A-1) above except that 300 ppm of a diacetyl gas was used instead of 750 ppm of an acetaldehyde gas.

(B) Metal Corrosiveness

A slurry containing 10% of deodorant composition was prepared using the deodorant composition and ion-exchanged water. Subsequently, 2 mL of slurry was placed in a square container (bottom area: 900 mm$^2$) produced from SUS304 foil or aluminum foil (both sizes were 100 mm×100 mm×0.01 mm) and heated and dried at a temperature of 130° C. for 1 hour. Then, a dry residue in the square container was removed. After the operation from the storage of the slurry in the square container to the removal of the dry residue was repeated a total of eight times, an inner surface of the container was visually observed, and the corrosiveness of the container was judged according to the following criteria.

⊙: No rust was observed even after eight times of repeated operations.

○: Rust was observed after three times of repeated operations, and very slight rust was observed after eight times of repeated operations.

x: Rust was observed in the first time of repeated operation, and significant rust was observed after eight times of repeated operations.

TABLE 1

| | | | Example | | | | | | | | | | | |
|---|---|---|---|---|---|---|---|---|---|---|---|---|---|---|
| | | | 1 | 2 | 3 | 4 | 5 | 6 | 7 | 8 | 9 | 10 | 11 |
| Deodorant composition | | Type | D1 | D2 | D3 | D4 | D5 | D6 | D7 | D8 | D9 | D10 | D11 |
| | Aminoguanidine salt (% by mass) | Aminoguanidine hydrochloride | 90 | 5 | 20 | 40 | 70 | 10 | 30 | 50 | | | |
| | | Aminoguanidine sulfate | | | | | | | | | 5 | 10 | 20 |
| | Chelating agent (% by mass) | Sodium hexametaphosphate | 10 | 0.5 | 2 | 5 | 10 | | | | 2 | | |
| | | Sodium dihydrogen phosphate | | | | | | 3 | | | | 2 | |
| | | Succinic acid | | | | | | | 3 | | | | 2 |
| | | Citric acid | | | | | | | | 3 | | | |
| | | EDTA·2 sodium | | | | | | | | | | | |
| | Inorganic carrier (% by mass) | Silica | | 94.5 | 78 | 55 | 20 | 87 | 67 | 47 | | | |
| | | Aluminum silicate | | | | | | | | | 93 | 88 | 78 |
| | | Zeolite | | | | | | | | | | | |
| Evaluation | Deodorizing capacity (ml/g) | Acetaldehyde | 93 | 11 | 44 | 79 | 89 | 22 | 66 | 99 | 10 | 20 | 34 |
| | | Diacetyl | 157 | 8 | 33 | 71 | 128 | 19 | 53 | 91 | 9 | 20 | 35 |
| | | Acetone | 171 | 8 | 39 | 74 | 132 | 19 | 59 | 95 | 7 | 18 | 38 |
| | | SUS corrosiveness | ○ | ○ | ◎ | ◎ | ◎ | ◎ | ◎ | ○ | ◎ | ◎ | ◎ |
| | | Al corrosiveness | ○ | ○ | ◎ | ◎ | ◎ | ◎ | ◎ | ○ | ◎ | ◎ | ◎ |

| | | | Example | | | | | Comparative Example | | |
|---|---|---|---|---|---|---|---|---|---|---|
| | | | 12 | 13 | 14 | 15 | 16 | 1 | 2 | 3 |
| Deodorant composition | | Type | D12 | D13 | D14 | D15 | D16 | D17 | D18 | D19 |
| | Aminoguanidine salt (% by mass) | Aminoguanidine hydrochloride | | | 10 | 20 | 30 | 100 | 20 | |
| | | Aminoguanidine sulfate | 30 | 40 | | | | | | 30 |
| | Chelating agent (% by mass) | Sodium hexametaphosphate | | | 1 | 5 | 10 | | | |
| | | Sodium dihydrogen phosphate | | | | | | | | |
| | | Succinic acid | | | | | | | | |
| | | Citric acid | 3 | | | | | | | |
| | | EDTA·2 sodium | | 3 | | | | | | |
| | Inorganic carrier (% by mass) | Silica | 67 | | | | | | 80 | |
| | | Aluminum silicate | | | | | | | | 70 |
| | | Zeolite | | 57 | 89 | 75 | 60 | | | |
| Evaluation | Deodorizing capacity (ml/g) | Acetaldehyde | 57 | 80 | 20 | 40 | 68 | 96 | 46 | 60 |
| | | Diacetyl | 50 | 68 | 18 | 35 | 55 | 175 | 38 | 56 |
| | | Acetone | 57 | 75 | 20 | 38 | 61 | 195 | 42 | 55 |
| | | SUS corrosiveness | ◎ | ◎ | ◎ | ◎ | ◎ | X | X | X |
| | | Al corrosiveness | ◎ | ◎ | ◎ | ◎ | ◎ | X | X | X |

INDUSTRIAL APPLICABILITY

The deodorant composition of the present invention is suitable for producing a deodorant filter, deodorant paper, a deodorant film, and the like, and can be contained in these products at a site handling a material that generates an aldehyde gas and/or a ketone gas from the product itself, for example, building materials, such as plywood boards, laminated wood materials, flooring materials, particle boards and heat insulating materials; floor carpets; noise reduction pads; cushion materials; car seats; headrests; armrests; door trims; molded ceilings; sun visors; rear package trays; instrument panels; dash insulator; and the like.

The invention claimed is:

1. A deodorant composition suitable for use with an aldehyde gas or a ketone gas, comprising:
    at least one aminoguanidine salt selected from an aminoguanidine hydrochloride and an aminoguanidine sulfate;
    a metal chelating agent; and
    an inorganic carrier;
    wherein the metal chelating agent and the at least one aminoguanidine salt are both supported by the inorganic carrier,
    a BET specific surface area of the inorganic carrier is 350 m$^2$/g or higher, and
    an average particle size of the inorganic carrier is from 0.02 μm to 20 μm.

2. The composition of claim 1, wherein the metal chelating agent is at least one selected from a group consisting of an inorganic phosphoric acid, a salt of an inorganic phosphoric acid, a carboxylic acid, and a salt of a carboxylic acid.

3. The composition of claim 1, wherein the inorganic carrier consists of a silicon compound.

4. The composition of claim 1, wherein the metal chelating agent is present in a range of from 1 to 50 parts by mass based on 100 parts by mass of the at least one aminoguanidine salt content.

5. The composition of claim 1, wherein the at least one aminoguanidine salt is present in a range of from 5% to 70% by mass with respect to the total composition mass.

6. The composition of claim 1, wherein the at least one aminoguanidine salt is an aminoguanidine hydrochloride.

7. The composition of claim 1, wherein the at least one aminoguanidine salt is an aminoguanidine sulfate.

8. The composition of claim 1, wherein the at least one aminoguanidine salt is a combination of an aminoguanidine hydrochloride and an aminoguanidine sulfate.

9. The composition of claim 1, wherein the metal chelating agent comprises at least one selected from the group consisting of an inorganic phosphoric acid, a salt of an inorganic phosphoric acid, a carboxylic acid, and a salt of a carboxylic acid.

10. The composition of claim 1, wherein the metal chelating agent comprises a salt of an inorganic phosphoric acid, a carboxylic acid, and a salt of a carboxylic acid.

11. The composition of claim 1, wherein the metal chelating agent comprises a carboxylic acid.

12. The composition of claim 1, wherein the metal chelating agent comprises a carboxylate salt.

* * * * *